(12) United States Patent
Altman

(10) Patent No.: US 7,412,028 B2
(45) Date of Patent: Aug. 12, 2008

(54) METHODS AND SYSTEM FOR MULTI-MODALITY IMAGING

(75) Inventor: Hernan Altman, Nesher (IL)

(73) Assignee: GE Medical Systems, Israel Ltd., Tirat Hacarmel (IL)

( * ) Notice: Subject to any disclaimer, the term of this patent is extended or adjusted under 35 U.S.C. 154(b) by 0 days.

(21) Appl. No.: 10/760,888

(22) Filed: Jan. 20, 2004

(65) Prior Publication Data

US 2005/0157839 A1    Jul. 21, 2005

(51) Int. Cl.
*A61B 6/03* (2006.01)
*G01T 1/166* (2006.01)

(52) U.S. Cl. .................. 378/63; 378/4; 250/363.04

(58) Field of Classification Search .............. 378/4, 378/19, 63
See application file for complete search history.

(56) References Cited

U.S. PATENT DOCUMENTS

| | | | |
|---|---|---|---|
| 5,719,401 A * | 2/1998 | Chaney et al. | 378/98.8 |
| 5,762,608 A * | 6/1998 | Warne et al. | 600/425 |
| 6,211,523 B1 * | 4/2001 | Gagnon | 250/363.04 |
| 6,242,743 B1 | 6/2001 | DeVito et al. | |
| 6,399,951 B1 | 6/2002 | Paulus et al. | |
| 6,408,050 B1 * | 6/2002 | Han et al. | 378/98.9 |
| 6,670,614 B1 * | 12/2003 | Plut et al. | 250/363.04 |
| 2002/0090050 A1 * | 7/2002 | Nutt et al. | 378/19 |
| 2003/0012331 A1 * | 1/2003 | Kojima et al. | 378/4 |
| 2003/0105397 A1 | 6/2003 | Turner et al. | |
| 2003/0128801 A1 | 7/2003 | Eisenberg et al. | |
| 2003/0141906 A1 | 7/2003 | Turner et al. | |
| 2003/0153828 A1 * | 8/2003 | Kojima et al. | 600/425 |
| 2003/0179853 A1 * | 9/2003 | Amemiya et al. | 378/63 |
| 2005/0017979 A1 * | 1/2005 | Sharma et al. | 345/504 |
| 2005/0023471 A1 * | 2/2005 | Wang et al. | 250/363.04 |

FOREIGN PATENT DOCUMENTS

JP    2000102529 A    *    4/2000

* cited by examiner

*Primary Examiner*—Chih-Cheng G Kao
(74) *Attorney, Agent, or Firm*—Dean D. Small; Small Patent Law Group

(57) ABSTRACT

A method for multi-modality imaging is provided. The method includes receiving a first signal from a detector operating in a first imaging modality, and receiving a second signal from the detector operating in a second imaging modality, wherein the first and second signals are received sequentially.

22 Claims, 2 Drawing Sheets

METHODS AND SYSTEM FOR MULTI-MODALITY IMAGING

BACKGROUND OF THE INVENTION

This invention relates generally to imaging systems capable of operation in multiple modalities, and more particularly to methods and systems for controlling the operation of multi-modality systems.

Multi-modality imaging systems are capable of scanning using different modalities, such as, for example, Positron Emission Tomography (PET), Single Positron emission tomography (SPECT), Computed Tomography (CT), Static X-Ray imaging, and Dynamic (Fluoroscopy) X-Ray imaging. In a multi-modality system (also referred to as a multi-modal system), a portion of the same hardware is utilized to perform different scans (e.g., an image produced by SPECT is processed and displayed respectively, by the same computer and display, as an image produced by CT). However, the data acquisition systems (also referred to as an imaging assembly) are different. For example, on a CT/SPECT system, a radiation source and a radiation detector are used in combination to acquire CT data, while a radiopharmaceutical is typically employed in combination with a SPECT camera to acquire SPECT data.

In multi-modality systems, such as, for example, an integrated SPECT/CT system, a single detector may be used to receive transmission image data in the form of x-ray photons and emission image data in the form of gamma ray photons. At least some known multi-modality systems attempt to detect and process image data from each different modality simultaneously. This method attempts to reduce imaging scan time by collecting and processing data from each modality simultaneously. However, the reduction realized by detecting and processing images from different modalities simultaneously may be only minimal because an emission scan typically takes several minutes, for example, approximately twenty minutes, and a transmission scan typically takes only several seconds, for example, approximately fifteen seconds.

During an emission portion of a scan, the multi-modality system detects and counts individual emission gamma photons at a relatively low rate, such as, only a few photons per pixel per second, and processes the gamma ray photons to determine an energy level of each gamma ray photon. During a transmission portion of a scan, the multi-modality system may operate a source of x-ray photons, such as an x-ray tube. The detector may be exposed to a relatively high x-ray photon flux from the x-ray source. However, a multi-modality system that attempts to perform an emission portion of the scan and the transmission portion of the scan simultaneously may receive x-ray photons at such a rate that signal conditioning electronics within the system cannot discriminate each x-ray photon received and may saturate or otherwise be damaged by the relatively high rate at which the x-ray photons are received.

BRIEF DESCRIPTION OF THE INVENTION

In one embodiment, a method for multi-modality imaging is provided. The method includes receiving a first signal from a detector operating in a first imaging modality, and receiving a second signal from the detector operating in a second imaging modality, wherein the first and second signals are received sequentially.

In another embodiment, a method of performing an image scan having at least a first scan portion and a second scan portion is provided. The method includes performing the first scan portion using a first modality, and performing the second scan portion using a second modality, wherein the first scan portion and second scan portion are performed sequentially.

In yet another embodiment, an imaging system is provided. The imaging system includes a detector configured to detect emission photons and transmission photons, a first processor coupled to the detector, wherein the first processor is configured to process emission photon data, and a second processor that is coupled to the detector, wherein the second processor is configured to process transmission photon data. The processing of emission photon data and processing transmission photon data is performed sequentially.

In still another embodiment, a controller for controlling a medical imaging system is provided. The controller includes a first processor configured to process emission photon data, and a second processor configured to process transmission photon data, wherein processing emission photon data and processing transmission photon data is performed sequentially.

DETAILED DESCRIPTION OF THE INVENTION

Figure 1:
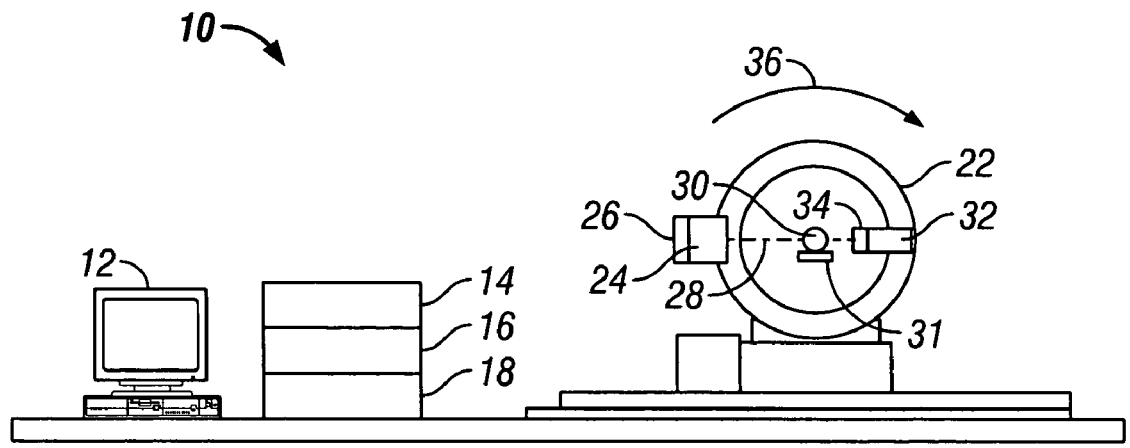
FIG. 1 is a schematic illustration of an imaging system in accordance with an exemplary embodiment of the present invention.

FIG. 1 is a schematic illustration of an exemplary embodiment of an imaging system 10. System 10 may include a controller work station, such as, a computer work station 12 that interfaces with a gantry motion controller 14, a patient bed motion controller 16 and an x-ray tube high voltage supply and controller 18. A rotating gantry 22 has a first radial arm 24 that includes an x-ray emitting source 26 mounted thereon. X-ray emitting source 26 is aligned such that x-rays emitted by x-ray emitting source 26 may be directed along an axis 28 toward an object 30. In the exemplary embodiment, object 30 is a human patient, reclining supine upon a patient bed 31. Object 30 may include a radiopharmecetical that concentrates in a predetermined region of object 30 and emits emission gamma rays (not shown in FIG. 1). Gantry 22 includes a second radial arm 32 that includes a CZT detector array 34 mounted thereon. As gantry 22 rotates in a direction 36, object 30 may be imaged with x-rays over a predetermined arc such that a plurality of image views are received, while object 30 remains positioned substantially directly between x-ray emitting source 26 and CZT detector array 34 and in alignment with respect to axis 28. A field of view of imaging system 10 may be established by a width of CZT detector array 34 in a plane of rotation. CZT detector array 34 may be translated in this plane to facilitate increasing an effective field of view of imaging system 10 during the rotation. CZT detector array 34 may be included in a plurality of imaging assembly modalities and/or multi-modality imaging assemblies, for example, any combination of a SPECT imaging assembly, a PET imaging assembly, a CT imaging assembly, a Static X-Ray imaging assembly, and a Dynamic (Fluoroscopy) X-Ray imaging assembly.

A collimator (not shown) may be positioned in front of detector array 34 to prevent scattered radiation from contributing to the image. When an x-ray CT image is acquired, x-ray emitting source 26 may be turned on and data from CZT detector array 34 may be output to computer work station 12 that may process the data and generate a tomographic image. Data from CZT detector array 34 may include, for example, pixel position, gantry angle of rotation and x-ray energy. CZT detector array 34 may include read-out electronics. Alternatively, x-ray emitting source 26 may be configured for continuous operation but, may include a shutter (not shown) to facilitate blocking x-rays from exiting x-ray emitting source 26.

When acquiring a SPECT image, x-ray emitting source 26 may be turned off or the shutter closed, and object 30 may be injected with a radioactive tracer compound that migrates to regions of interest within object 30. Gamma rays emitted by the radioactive tracer compound are received by CZT detector array 34, and the gamma ray pixel position, gantry angle, and gamma-ray energy data may be transmitted to computer work station 12 for image generation. A collimator in front of CZT detector array 34 may facilitate ensuring that only gamma-rays that are emitted normal to the detector, or along another predetermined set of projection angles, contribute to the energy received.

An X-ray CT and SPECT image may be sequentially acquired if x-ray emitting source 26 is switched on, such that x-rays from x-ray emitting source 26 only reach CZT detector array 34 during a CT scan, and during a SPECT scan, x-ray emitting source 26 is switched off or a shutter is moved in place to block substantially all x-rays from x-ray emitting source 26 from reaching CZT detector array 34. The CT and SPECT image data may be processed by separate processors that are configured to facilitate processing the particular energy level and rate of receipt of photons from each modality.

Figure 2:
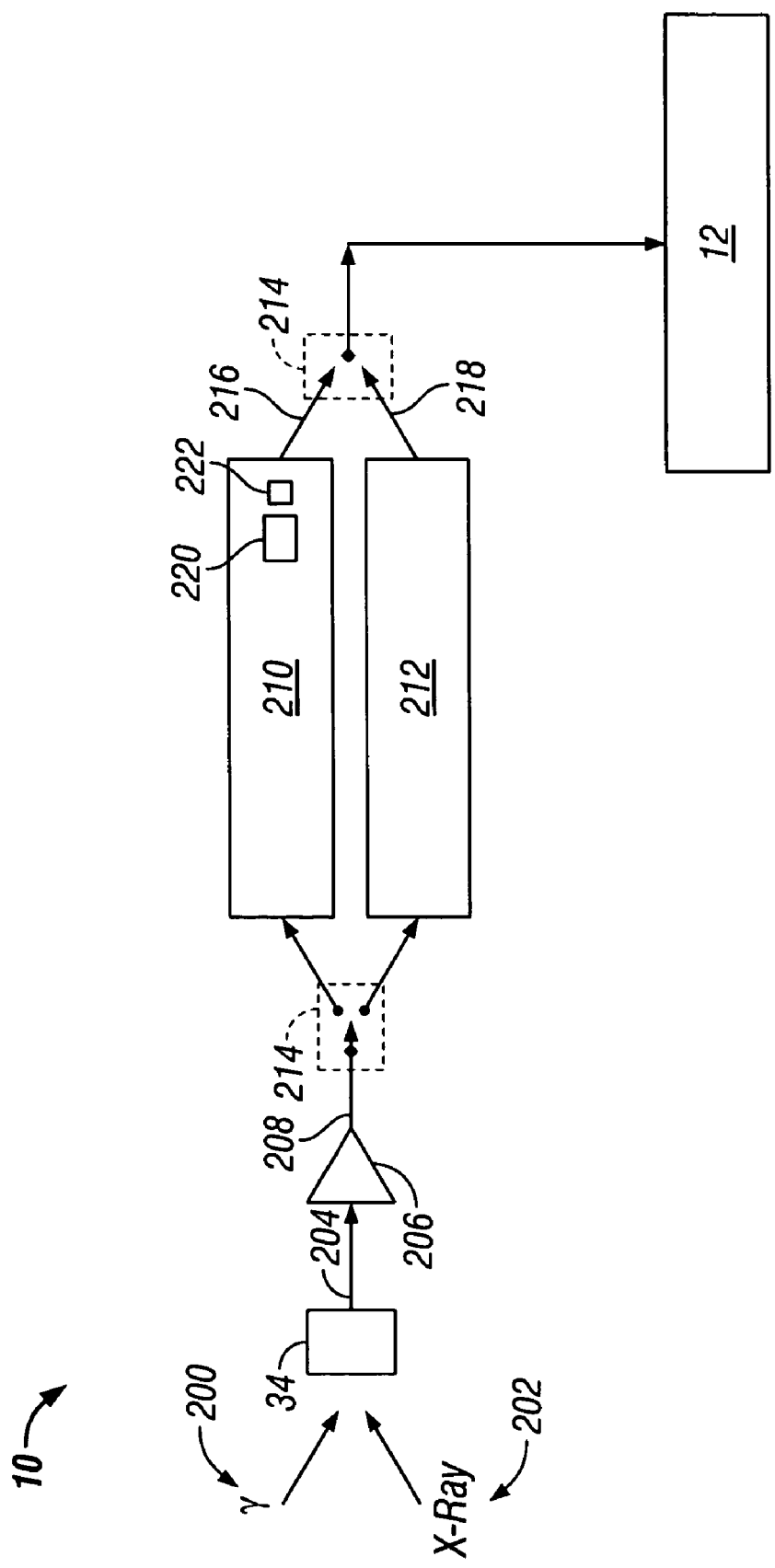
FIG. 2 is a block diagram of an exemplary embodiment of the imaging system shown in FIG. 1.

FIG. 2 is a block diagram of an exemplary embodiment of imaging system 10 (shown in FIG. 1). Imaging system 10 includes detector array 34, such as a CZT detector array that is capable of receiving transmission x-ray photons 202, and receiving and discriminating emission gamma ray photons 200. An output 204 of CZT detector array 34 is coupled to a pre-amplifier 206. An output 208 of pre-amplifier 206 is selectively coupled to a transmission photon signal electronics circuit, such as a processor 210 and an emission photon signal electronics circuit, such as a processor 212 through a switch 214, which also may simultaneously control x-ray emitting source 26 (shown in FIG. 1), such that x-ray emitting source 26 only emits x-rays when transmission photon signal processor 210 is selected via switch 214. For example, switch 214 may control energization of high voltage power to x-ray emitting source 26 during a transmission portion of a scan. Switch 214 may also control a substantially x-ray opaque shutter to block x-rays from leaving x-ray emitting source 26. In the exemplary embodiment, switch 214 is a double-throw switch having a plurality of poles. In an alternative embodiment, switch 214 may be a software switch or relay, or any other suitable switching member or device. An output 216 of transmission photon signal processor 210 may be coupled to workstation 12 through a contact pair of switch 214. An output 218 of emission photon signal processor 212 may also be coupled to workstation 12 through a contact pair of switch 214. Switch 214 may be actuated in response to a manual input from a user, a control signal from work station 12, or may be actuated in response to a count rate seen by CZT detector array 34. For example, CZT detector array 34 may only see a small number of photons due to x-ray emitting source 26 being in an "off" state or due to an x-ray opaque shutter blocking substantially all transmission photons from impinging on CZT detector array 34, therefore switch 214 may be controlled to couple the output of CZT detector array 34 to emission photon signal processor 212. Similarly, CZT detector array 34 may see a relatively large number of photons due to x-ray emitting source 26 being in an "on" state or due to the x-ray opaque shutter being moved such that substantially all transmission photons that have passed through object 30 may be impinging on CZT detector array 34, therefore switch 214 may be controlled to couple the output of CZT detector array 34 to transmission photon signal processor 210.

In operation, emission gamma ray photons 200 emitted from object 30 may have an energy in a range of approximately seventy kilo electron-volts (keV) to approximately six hundred keV, and transmission x-ray photons 202 may have an energy in a range of approximately twenty keV to approximately one-hundred keV. Additionally, a flux magnitude of transmission x-ray photons 202 may be approximately one-thousand times greater than a flux magnitude of emission gamma ray photons 200. Accordingly, CZT detector array 34 is capable of detecting and discriminating the energy of each emission gamma ray photon 200, and CZT detector array 34 is capable of detecting a presence of relatively high flux of relatively low energy transmission x-ray photons. Such high flux may saturate and/or damage emission photon signal processor 212.

In the exemplary embodiment, CZT detector array 34 is used during both an emission portion of a scan and a transmission portion of the scan, and a respective signal from each portion of the scan is processed through a separate electronics circuit configured to optimally process each respective signal. During the emission portion of the scan, x-ray emitting source 26 is "off", such that substantially no transmission x-ray photons 202 are emitted towards object 30 along axis 28. A signal relative to emission gamma ray photons 200 detected by CZT detector array 34 may be transmitted to emission photon signal processor 212 that is capable of detecting and counting individual gamma photon at a low rate (e.g. a few photons per pixel per second). In the exemplary embodiment, emission photon signal processor 212 is capable of performing relatively accurate energy discrimination of each detected emission gamma ray photon 200.

During the transmission portion of the scan, x-ray emitting source 26 is "on" such that x-rays of a predetermined energy and flux are emitted towards object 30 along axis 28. In the exemplary embodiment, x-ray emitting source 26 is an x-ray tube that is intermittently energized wherein x-ray emitting source 26 is "on" when the x-ray tube is receiving power. In an alternative embodiment, x-ray emitting source 26 may be energized continuously and a flux of transmission x-ray photons 202 is determined by a position of a shutter, which substantially blocks transmission x-ray photons 202 in a first position, and allows passage of transmission x-ray photons 202 in a second position. A signal relative to transmission x-ray photons 202 detected by CZT detector array 34 may be transmitted to transmission photon signal processor 210 that is capable of withstanding a relatively high current in CZT detector array 34 when it is exposed to a relatively high flux of transmission x-ray photons 202. In the exemplary embodiment, transmission photon signal processor 210 operates in a "current mode" wherein a charge resulting from substantially all transmission x-ray photons 202 impinging on CZT detector array 34 at a given time is integrated. In an alternative embodiment, transmission photon signal processor 210 operates in a "fast counting mode" wherein a high speed triggering unit 220 triggers a counter 222 each time a transmission x-ray photon 202 having at a predetermined amount of energy is detected. Counter 222 may accumulate a number of trigger firings in a given time. In another alternative embodiment, transmission photon signal processor 210 is capable of discriminating the energy of each individual transmission x-ray photon 202. Transmission photon signal processor 210 may also include circuitry (not shown) that corrects for the emission gamma photons that impinge on CZT detector array 34 during the transmission portion of the scan.

In the exemplary embodiment, work station 12 receives a transmission image data set from transmission photon signal processor 210 and an emission image data set from emission photon signal processor 212 sequentially. For example, a scan may include an emission portion and a transmission portion wherein the emission portion is completed, and then the transmission portion of the scan is performed. In an alternative embodiment, the emission portion includes a plurality of views that are less than a complete emission portion of the scan, and the transmission portion includes a plurality of views that are less than a complete transmission portion of the scan. In this embodiment, the emission portion and transmission portion alternate at each view to complete the views sequentially until a scan is completed. Work station 12 may then combine and process each image data set separately and thereafter convolve the generated images into a combined emission and transmission image. Transmission image data may also include emission image data due to emission gamma photons being present during both the transmission portion of the scan and the emission portion of the scan. Accordingly, work station 212 may be programmed to correction transmission image data to account for emission image data that may be collected during the transmission portion of the scan.

In an alternative embodiment, each of transmission photon signal processor 210 and emission photon signal processor 212 may transmit respective image data sets to respective separate processors (not shown) that each generate an object image from the image data set received. Each of the transmission photon signal processor 210 and emission photon signal processor 212 may transmit respective object images to work station 12 either substantially simultaneously, or sequentially wherein work station 12 may then convolve the respective object images into a combined emission and transmission image.

Figure 3:
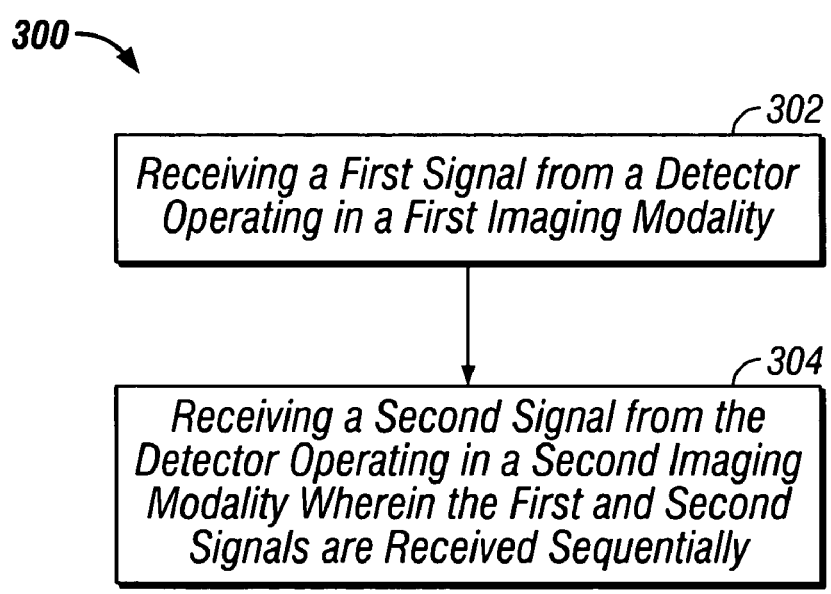
FIG. 3 is a flow chart of an exemplary method for multi-modality imaging that may be used with the imaging system shown in FIG. 1.

FIG. 3 is a flow chart of an exemplary method 300 of examining an object, such as a patient, that may be used with imaging system 10 (shown in FIG. 1). Method 300 includes receiving 302 a first signal from a detector operating in a first imaging modality. The first signal represents an image of an object from at least one of a plurality of views of the object using the first imaging modality, or represents an image of the object from a scan of the object using the first imaging modality. System 10 also includes receiving 304 a second signal from the detector operating in a second imaging modality. The second signal represents an image of an object from at least one of a plurality of views of the object using the second imaging modality, or represents an image of the object from a scan of the object using the second imaging modality. In the exemplary embodiment, the first and second signals are received sequentially. The term, sequentially, as used herein, describes completing at least a first portion of a scan, such as a view, or performing a complete scan portion using a first modality and thereafter performing at least a second portion of a scan, such as a view, or a complete scan portion using a second modality. Accordingly, a scan may be performed sequentially by completing a first scan portion using a first modality and then completing a second scan portion using a second modality, wherein a complete scan may comprise multiple scan portions. Alternatively, a scan may also be performed sequentially by completing a first view using a first modality, then completing a second view using a second modality, and then alternating modalities at each successive view until a scan in completed. A technical effect of method 300 is reducing a degradation of image quality of a multi-modality scan image by coupling an electronics circuit that is optimized to the respective modality during each scan portion with only a minimal additional scan time.

It is contemplated that the benefits of the invention accrue to all multi-modality imaging systems, such as, for example, but not limited to, a CT/SPECT imaging system.

The above-described multi-modality imaging systems provide a cost-effective and reliable means for examining an object, such as, for example, a patient. More specifically, each imaging system includes a detector configured to detect image data from a plurality of modalities, and at least one photon signal electronics circuit that is capable of detecting and determining a number of individual photons at a low rate, such as by counting, and operating in a "current mode" or a "fast counting mode". Image data is acquired sequentially such that the electronics may be optimized to process image data for each respective modality. As a result, an imaging system is provided that permits multi-modality imaging while facilitating minimizing image degradation resulting from processing transmission image data with electronics that also must be able to process emission image data simultaneously.

Exemplary embodiments of multi-modality imaging systems are described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems.

While the invention has been described in terms of various specific embodiments, those skilled in the art will recognize that the invention can be practiced with modification within the spirit and scope of the claims.

What is claimed is:

1. A method for multi-modality imaging with a cadmium zinc telluride (CZT) detector array, the method comprising:
   receiving a first signal during a first portion of an imaging scan from the entire cadmium zinc telluride (CZT) detector array operating in a first imaging modality;
   receiving a second signal during a second portion of the imaging scan from the entire CZT detector array operating in a second imaging modality;
   wherein the first and second signals are received sequentially during respective portions of the imaging scan;
   wherein the imaging scan is performed sequentially by completing a first single view angle using the first imaging modality, then completing a second single view angle using the second imaging modality, and then alternating the modalities at each successive single view angle until the imaging scan is completed;
   processing emission photons impinging on the entire CZT detector array in the first imaging modality and processing transmission photons impinging on the entire CZT detector array in the second imaging modality.

2. A method in accordance with claim 1 further comprising processing the first signal using a first processor configured to process image data of the first imaging modality.

3. A method in accordance with claim 1 further comprising processing the second signal using a processor configured to process image data of the second imaging modality.

4. A method in accordance with claim 1 further comprising switching between a first processor and a second processor for processing the first and second signals.

5. A method in accordance with claim 1 further comprising selecting one of a first and second processor for processing the first and second signals, based upon the modality.

6. A method in accordance with claim 1 further comprising operating an x-ray source when receiving a first signal from the detector array operating in the first imaging modality.

7. A method in accordance with claim 1 further comprising removing an x-ray source from operation when receiving the first signal from the detector array operating in the first imaging modality.

8. A method of performing an image scan having at least a first scan portion and a second scan portion with a CZT detector array, said method comprising:
performing the first scan portion using a first modality with the entire CZT detector array;
performing the second scan portion using a second modality with the entire CZT detector array;
wherein the first scan portion and second scan portion are performed alternately during the scan;
wherein the image scan is performed sequentially by completing a first single view angle using the first modality, then completing a second single view angle using the second modality, and then alternating the modalities at each successive single view angle until the image scan is completed;
using at least one processor in a current mode to process x-ray image data; and
using at least one processor in a discriminate mode to process gamma ray image data wherein the processor in the discriminate mode is configured to determine an energy of each gamma ray.

9. A method in accordance with claim 8 wherein performing the first scan portion using a first modality comprises performing the first scan portion using at least one of a SPECT imaging modality and a PET imaging modality.

10. A method in accordance with claim 8 wherein performing the second scan portion using a second modality comprises performing the second scan portion using at least one of a CT imaging modality, a Static X-Ray imaging modality, and a Dynamic (Fluoroscopy) X-Ray imaging modality.

11. A method in accordance with claim 8 further comprising:
using the detector array to receive emission image data during the first scan portion; and
using the detector array to receive transmission image data during the second scan portion.

12. A method in accordance with claim 8 further comprising:
using a first processor to process emission image data during the first scan portion; and
using a second processor to process transmission image data during the second scan portion.

13. A method in accordance with claim 8 further comprising operating an x-ray source when processing transmission image data.

14. An imaging system comprising:
a CZT detector array comprising a plurality of detectors configured to detect emission photons during a first portion of a scan in a first imaging modality with the entire detector array and transmission photons during a second portion of the scan in a second imaging modality with the entire detector array;
a first processor coupled to said detector array, said first processor configured to process emission photon data;
a second processor coupled to said detector array, said second processor configured to process transmission photon data;
wherein processing emission photon data from said CZT detector array and processing transmission photon data from said CZT detector array is performed sequentially during the scan; and wherein the scan is performed sequentially by completing a first single view angle using the first imaging modality, then completing a second single view angle using the second imaging modality, and then alternating the modalities at each successive single view angle until the scan is completed.

15. An imaging system in accordance with claim 14 wherein each of said plurality of CZT detectors is configured to operate in at least two of a SPECT imaging modality, a PET imaging modality, a CT imaging modality, a Static X-Ray imaging modality, and a Dynamic (Fluoroscopy) X-Ray imaging modality.

16. An imaging system in accordance with claim 14 configured to selectively operate an x-ray source.

17. An imaging system in accordance with claim 14 wherein said first processor and said second processor are selectively operable.

18. An imaging system in accordance with claim 14 further comprising a shutter configured to facilitate preventing said first processor from receiving transmission image data.

19. An imaging system in accordance with claim 14 wherein said first processor is configured to operate in a discriminate mode.

20. An imaging system in accordance with claim 14 wherein said second processor is configured to operate in a current mode.

21. A controller for controlling a medical imaging system with a CZT detector array comprising:
a first processor configured to process emission photon data received from the entire CZT detector array during a first portion of a scan in a first imaging modality;
a second processor configured to process transmission photon data received from the entire CZT detector array during a second portion of the scan in a second imaging modality;
wherein processing emission photon data from all detectors participating in the scan and processing transmission photon data from all detectors participating in the scan is performed sequentially during the scan; and wherein the scan is performed sequentially by completing a first single view angle using the first imaging modality, then completing a second single view angle using the second imaging modality, and then alternating the modalities at each successive view angle until the scan is completed.

22. A controller in accordance with claim 21 wherein said first and second processors are configured for operation in combination with a medical imaging system operating in at least two of a SPECT imaging modality, a PET imaging modality, a CT imaging modality, a Static X-Ray imaging modality, and a Dynamic (Fluoroscopy) X-Ray imaging modality.

* * * * *

UNITED STATES PATENT AND TRADEMARK OFFICE
CERTIFICATE OF CORRECTION

PATENT NO. : 7,412,028 B2
APPLICATION NO. : 10/760888
DATED : August 12, 2008
INVENTOR(S) : Hernan Altman It is certified that error appears in the above-identified patent and that said Letters Patent is hereby corrected as shown below:

Col. 7-8, lines 61-17; should read;
14. An imaging system comprising:
a CZT detector array comprising a plurality of detectors configured to detect emission photons during a first portion of a scan in a first imaging modality with the entire detector array and transmission photons during a second portion of the scan in a second imaging modality with the entire detector array;
a first processor coupled to said detector array, said first processor configured to process emission photon data;
a second processor coupled to said detector array, said second processor configured to process transmission photon data; wherein processing emission photon data from said CZT detector array and processing transmission photon data from said CZT detector array is performed sequentially during the scan; and wherein the scan is performed sequentially by completing a first single view angle using the first imaging modality, then completing a second single view angle using the second imaging modality, and then alternating the modalities at each successive single view angle until the scan is complete.

Signed and Sealed this

Eleventh Day of November, 2008

JON W. DUDAS
*Director of the United States Patent and Trademark Office*

UNITED STATES PATENT AND TRADEMARK OFFICE
CERTIFICATE OF CORRECTION

PATENT NO. : 7,412,028 B2  Page 1 of 1
APPLICATION NO. : 10/760888
DATED : August 12, 2008
INVENTOR(S) : Hernan Altman It is certified that error appears in the above-identified patent and that said Letters Patent is hereby corrected as shown below:

Column 7, line 61 thru Column 8, line 17, should read;
14. An imaging system comprising:
a CZT detector array comprising a plurality of detectors configured to detect emission photons during a first portion of a scan in a first imaging modality with the entire detector array and transmission photons during a second portion of the scan in a second imaging modality with the entire detector array;
a first processor coupled to said detector array, said first processor configured to process emission photon data;
a second processor coupled to said detector array, said second processor configured to process transmission photon data; wherein processing emission photon data from said CZT detector array and processing transmission photon data from said CZT detector array is performed sequentially during the scan; and wherein the scan is performed sequentially by completing a first single view angle using the first imaging modality, then completing a second single view angle using the second imaging modality, and then alternating the modalities at each successive single view angle until the scan is complete.

This certificate supersedes the Certificate of Correction issued November 11, 2008.

Signed and Sealed this

Ninth Day of December, 2008

JON W. DUDAS
*Director of the United States Patent and Trademark Office*